United States Patent
Thomas et al.

(10) Patent No.: US 6,840,121 B2
(45) Date of Patent: Jan. 11, 2005

(54) SELF-POWERED FLUID SAMPLER

(75) Inventors: Ray Gerald Thomas, Gainesville, FL (US); Jonathan Bowman Martin, Gainesville, FL (US); Kevin Martin Hartl, Gainesville, FL (US)

(73) Assignee: University of Florida Reasearch Foundation, Inc., Gainesville, FL (US)

( * ) Notice: Subject to any disclaimer, the term of this patent is extended or adjusted under 35 U.S.C. 154(b) by 0 days.

(21) Appl. No.: 10/622,747

(22) Filed: Jul. 18, 2003

(65) Prior Publication Data

US 2004/0123681 A1 Jul. 1, 2004

Related U.S. Application Data

(60) Provisional application No. 60/397,116, filed on Jul. 18, 2002.

(51) Int. Cl.[7] .............................. G01N 1/10; G01N 1/14
(52) U.S. Cl. ................ 73/863.31; 73/863.32; 73/863.81; 73/863.86; 73/864.01; 73/864.13
(58) Field of Search .................. 73/863.01, 863.23, 73/863.31, 863.32, 863.33, 863.81, 863.83, 863.84, 863.86, 864.01, 864.13, 864.14

(56) References Cited

U.S. PATENT DOCUMENTS

| | | | | |
|---|---|---|---|---|
| 3,176,517 A | * | 4/1965 | Chelminski | 73/864.62 |
| 3,339,417 A | * | 9/1967 | Richard | 73/863.31 |
| 3,513,709 A | * | 5/1970 | Pullos | 73/863.01 |
| 3,537,316 A | * | 11/1970 | Stewart et al. | 73/170.33 |
| 3,751,983 A | * | 8/1973 | Rutkowski et al. | 73/864.35 |
| 3,884,081 A | * | 5/1975 | Griffith | 73/863.31 |
| 3,921,456 A | * | 11/1975 | Newcomb et al. | 73/863.31 |
| 4,046,012 A | * | 9/1977 | Studenick | 73/863.33 |
| 4,116,067 A | * | 9/1978 | Pankratz et al. | 73/863.31 |
| 4,458,544 A | * | 7/1984 | Gyer et al. | 73/864.21 |
| 4,744,955 A | * | 5/1988 | Shapiro | 134/100.1 |
| 4,801,434 A | * | 1/1989 | Kido et al. | 422/100 |
| 5,113,711 A | * | 5/1992 | Davloor et al. | 73/864.63 |
| 5,293,934 A | * | 3/1994 | Burge et al. | 166/202 |
| 5,319,986 A | * | 6/1994 | Padden et al. | 73/863.21 |
| 5,404,763 A | * | 4/1995 | Guggenheim | 73/863.31 |
| 5,553,508 A | * | 9/1996 | Dabberdt et al. | 73/863.02 |
| 6,187,530 B1 | * | 2/2001 | Scholin et al. | 435/4 |
| 6,612,111 B1 | * | 9/2003 | Hodges et al. | 60/583 |

* cited by examiner

Primary Examiner—Hezron Williams
Assistant Examiner—David A. Rogers
(74) Attorney, Agent, or Firm—Akerman Senterfitt

(57) ABSTRACT

An automatic fluid sampler includes a substantially watertight housing and a structure for drawing fluid from outside the housing, wherein the fluid drawing structure is powered by stored potential energy within the housing. A method of automatic fluid sampling employs such samplers, and a fluid sampling system includes a plurality of interconnected samplers.

20 Claims, 2 Drawing Sheets

SELF-POWERED FLUID SAMPLER

CROSS-REFERENCE TO RELATED APPLICATION

This application claims the benefit of U.S. Provisional Patent Application Ser. No. 60/397,116 entitled "Submersible Fluid Sampler," filed Jul. 18, 2002, the entirety of which is incorporated herein by reference.

STATEMENT AS TO FEDERALLY SPONSORED RESEARCH OR DEVELOPMENT

This invention was made with U.S. Government support under grant No. 1610-615-12 awarded by the National Science Foundation. The U.S. Government may have certain rights in the invention.

FIELD OF THE INVENTION

The invention pertains to a fluid sampler. More particularly, the invention relates to a submersible self-powered fluid sampler suited for use in remote environments.

BACKGROUND

Fluid sampling can be used to effectively monitor environmental changes in water, air, or other desired fluids. For example, fluid sampling may be used to monitor water quality in ground water, lake water, and ocean water. The taking of samples may be desired over extended periods of time, on varying days, at various depths and/or in remote locations.

Many dynamic problems in hydrology, hydrogeology, and hydrogeochemistry can be addressed through detailed spatial mapping and time series measurements of the chemical and isotopic composition of water. For example, frequent and detailed water sampling may be required to understand the environmental variables that control mixing of surface and ground water, the isotopic and chemical composition of lake water, nutrient loading in estuaries and the isotopic and chemical composition of ocean water.

The need for broadly-spaced simultaneous and/or high frequency sampling, however, can result in complication and expense. Sampling can be simplified by collecting fluids of interest, for example water, using automatic samplers. Existing automatic samplers are designed predominantly for use in developed water systems, such as storm sewers and water treatment plants, which can be visited frequently. Available automatic samplers are generally not suitable for use in remote areas for several reasons. First, they do not preserve the water samples taken. For example, they generally do not prevent evaporation. This can prevent their deployment in remote areas which necessitate sampling and storage of multiple samples over an extended period of time, for example for a period of years.

In addition, many presently available automatic sampling devices are unsuitable for deployment in remote and/or deep bodies of water because they are not self contained. For example, U.S. Pat. No. 4,288,206 to Tigwell, et al. discloses a water sampler that uses multiple glass chambered syringes to collect water samples to be delivered under pressure to an external testing site, such as to a sorption column. Other such devices include components, such as a pump and sample bottles, that remain onshore. Sample collection is achieved through a tube that is extended into the water to be sampled. Accordingly, the sampling range of these devices is generally restricted to the length of the sampling hoses.

Examples of fluid samplers designed to be submersible, include U.S. Pat. No. 4,462,265 to Rein, which discloses a water sampling system for use with a ship. A mechanically powered unit equipped with a pump is lowered to a desired depth to withdraw water samples. Samples are then drawn into several collection devices placed at various depths between the unit and the ship. The pump is powered by towing movements of the ship. The invention has limited applications since it requires continuous presence at the monitoring site and is not automatic.

Other currently available samplers allow for automatic sampling, but require the use of motors and pumps to acquire the desired samples. For example, U.S. Pat. No. 5,606,138 to Saarenketo discloses a water sampling device that allows automatic sampling without the need for continuously manning the monitoring site. An electric motor and a centrifugal pump are placed in connection with a sample container to take samples of specific volumes of water at specific intervals. However, the unit resides in a buoyant container and therefore is not designed for submersion. Furthermore, the requirement of a motor and pump reduces reliability and adds additional weight and cost to the sampler.

SUMMARY OF THE INVENTION

The invention provides an inexpensive submersible automatic fluid sampler that is self-powered and suitable for continuous unmanned use in remote locations over extended periods of time. Sample collection is triggered by the release of stored potential energy contained within the sampler, for example by the potential energy of a compressed spring held under a vacuum, that is released upon opening of a valve that seals the sample collection chamber. Use of stored potential energy as the source of power to drive sample collection advantageously minimizes the energy requirements for sample collection, rendering the device suitable for long-term use, for example, in locations removed from external sources of power.

Accordingly, the invention provides in one aspect a fluid sampler that includes a substantially watertight housing, and a structure contained at least partially within the housing for drawing fluid from outside the housing into the housing. The structure for drawing fluid is powered by stored potential energy within the housing.

In some versions of the fluid sampler, the stored potential energy can be mechanical potential energy contained in a compressed spring. The structure for drawing fluid in the fluid sampler can include at least one spring-loaded syringe operably connected to at least one solenoid valve. The structure for drawing fluid can further include at least one filter assembly.

In embodiments containing spring-loaded syringes and solenoid valves, the fluid sampler can further include a control device adapted for issuing electronic activating signals. Activating signals applied to the solenoid valve result in fluid being drawn into the fluid-drawing structure.

The control device in the fluid sampler can be microprocessor or a microcomputer. The fluid sampler can also include an electronic memory and a clock. Some versions of the fluid sampler can be equipped with at least one sensor communicably connected to the microcomputer or microprocessor. Sensors can include a pH sensor, a temperature sensor, a dissolved oxygen probe, a conductivity sensor, a salinity sensor or an ion selective electrode. In some versions of the sampler equipped with a sensor, fluid collection can be initiated by a signal from the sensor.

In embodiments of the sampler including a memory, the microprocessor or microcomputer can process and store information from the sensor. The stored information can include environmental conditions present and the time of fluid sampling.

Certain embodiments of the fluid sampler can include at least one antenna adapted for receiving a wireless activating signal and can further include a receiving device connected to the antenna adapted to receive wireless transmissions from outside of the sampler. In some versions, the receiving device can be a transceiver for sending wireless signals to at least one other location outside of the housing.

In another aspect, the invention provides a fluid sampling system including a plurality of fluid samplers, each including a substantially watertight housing, and a structure contained at least partially within the housing for drawing fluid from outside of the housing into the housing, wherein the structure for drawing fluid is powered by stored potential energy within the housing. At least one of the plurality of fluid samplers can be a master sampler including at least one antenna and a transceiver connected to the antenna. In some versions, the master sampler can relay instructions to and from other fluid samplers using wire or fiber optic connections.

The invention further provides a method for sampling fluid including the steps of providing a substantially watertight housing and structure contained at least partially within the housing for drawing fluid from outside of the housing into the housing, the structure for drawing fluid being powered by stored potential energy within the housing, and drawing the fluid into the housing using the stored potential energy.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

The invention provides a fluid sampler that includes a substantially watertight housing, and a structure contained at least partially within the housing for drawing fluid from outside the housing. Fluid, once within the housing, is sealed. Accordingly, drawn fluid can be stored for extended periods, such as years.

As used herein, "substantially watertight" refers to the ability of the housing to repel water to at least the extent required to support the operation of electronic circuitry disposed within the housing for a desired minimum time period. As known to those skilled in the art, increasing submersion depths require higher levels of watertight integrity.

Although described generally as a fluid sampler, which would typically operate submerged in a body of water, the sampler can be applied to sample other fluids, including air. If embodied as an air sampler, the housing is preferably airtight.

The structure for drawing fluid is powered by stored potential energy within the sampler, rather than requiring energy to be supplied to the system to draw fluid, as in other sampling systems. The stored potential energy can be mechanical energy in the form of compressed spring. In certain embodiments of the fluid sampler using stored mechanical energy, the structure for drawing fluid can include at least one spring-loaded syringe operably connected to at least one solenoid valve that seals the fluid drawing structure from the outside environment. The fluid sampler can further include a control device for issuing electronic activating signals to the solenoid valve in the syringe. The solenoid valve is normally in the closed position. Application of the activating signal to the solenoid valve causes the valve to open, resulting in fluid being drawn into the structure for drawing fluid.

Figure 1:
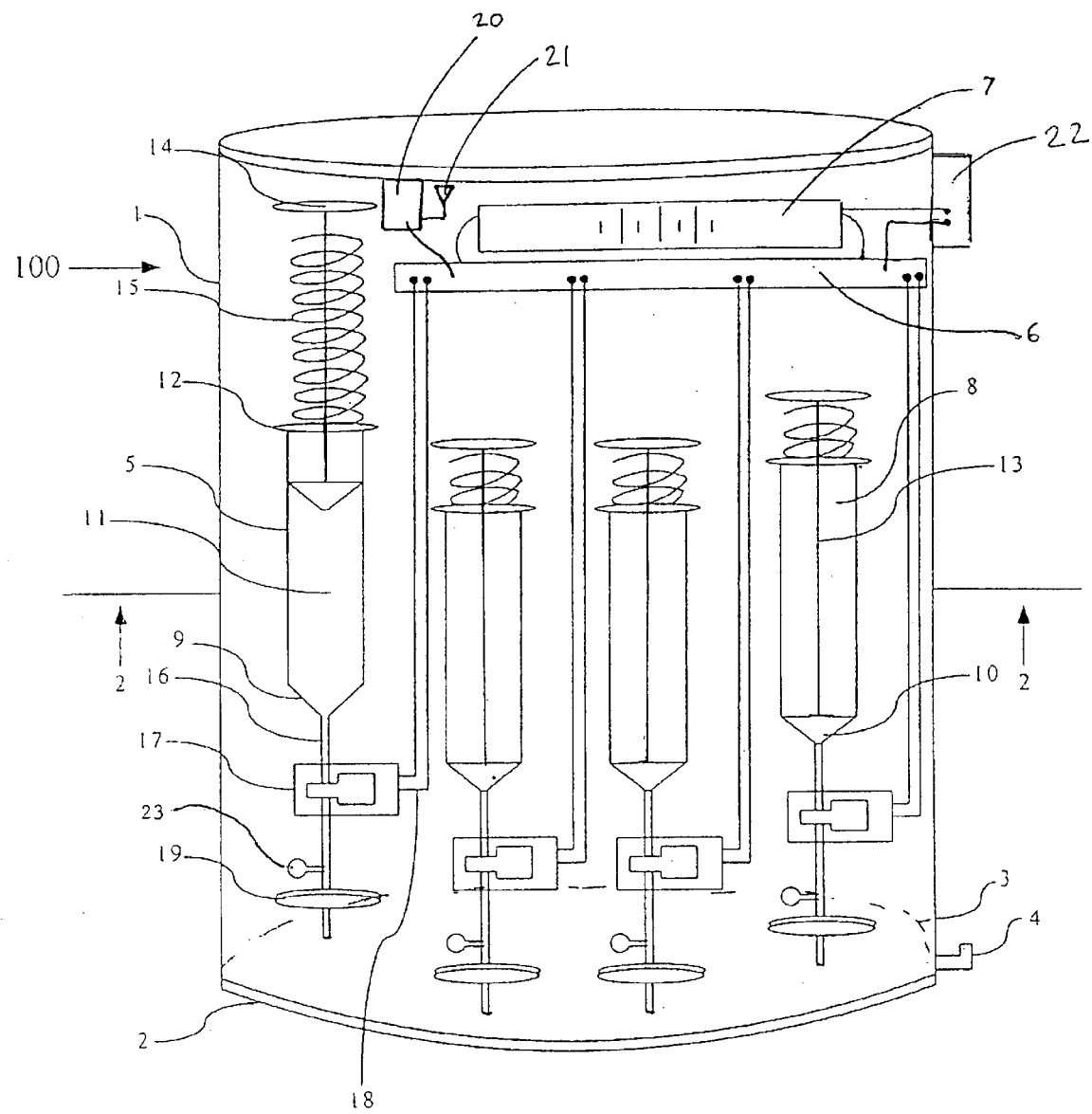
FIG. 1 is an elevation view of a fluid sampler including a plurality of syringes, with one syringe filled and other syringes unfilled, according to an embodiment of the invention.

An exemplary embodiment of a fluid sampler 100 adapted for obtaining liquid samples is illustrated in FIG. 1. Fluid sampler 100 includes at least a substantially watertight container comprising housing 1 and at least one structure for drawing fluid 5 therein. The fluid to be sampled can be, for example, water, such as from man-made constructions, groundwater, an estuary, a river, a lake, or an ocean.

Housing 1 is shown as being substantially cylindrical. However, housing 1 can be any shape, such as square. Housing 1 is preferably formed from a non-porous and moldable material. Most plastics can generally be used for this purpose. Deep deployments, such as ocean waters, generally require higher-strength and non-corrosive materials, such as titanium, ceramic, and certain composite materials.

Fluid sampler 100 preferably includes a removable base 2, which together with housing 1 forms at least a substantially watertight seal. The removable base 2 can attach to the bottom wall 3 of the housing 1 secured using at least one latch 4. Removable base 2 permits access to fluid sampler 100 for later retrieval of drawn samples or for servicing fluid sampler 100. If desired, however, other embodiments of the invention can be made without a removable base.

Structure for drawing fluid 5 can be any structure which includes a volume that can be filled with fluid without the need for an active device, such as a motor or pump. For example, one or more syringes 5 for drawing fluid can be positioned inside housing 1. Syringes 5 preferably include a spring 15, and are thus adapted to be spring-loaded. In the embodiment shown in FIG. 1, syringe 5 includes an internal cavity 8, and a stopper 10 which has the same size and fit as the syringe bottom 9. An internal syringe reservoir 11 for containing fluid drawn into the syringe is created within internal cavity 8 between the syringe bottom 9 and the stopper 10. Attached to the stopper 10 is an internal rod 13, located partly within the internal cavity 8 above the stopper 10, and extending outside the syringe top 12. Connecting to the portion of the internal rod 13 extending away from the stopper 10 is a mounting base 14. While the connection between the stopper 10 and mounting base 14 shown in FIG. 1 is a rod 13, any substantially rigid connector of any size or shape can be used. Also, while the mounting base 14 shown in FIG. 1 is circular, any size or shape for base 14 can be used.

The volume held by each syringe 5 can be selected based on the intended application. For example, a typical commercially available syringe can hold a volume of approximately 60 cubic centimeters ($cm^3$). Although 60 $cm^3$ is generally sufficient for most analyses, several syringes could be triggered simultaneously in order to increase the volume of water collected at a given instant of time. Alternatively, different sized syringes (larger or smaller) could be specially manufactured and used with fluid sampler 100.

Figure 2:
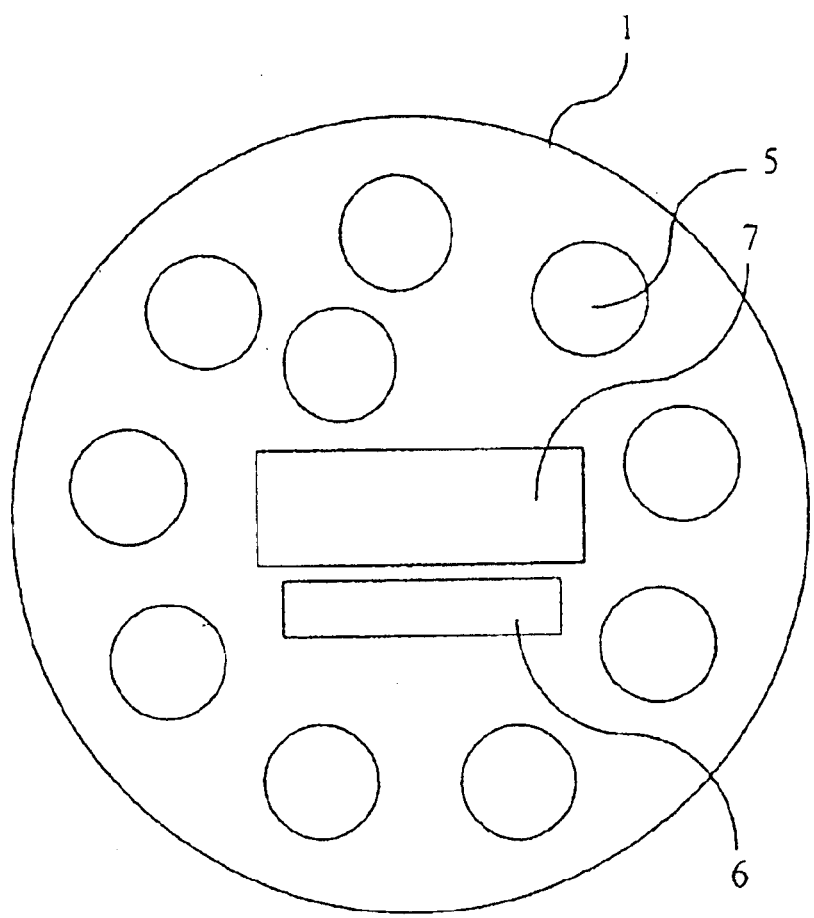
FIG. 2 is a view of the sampler taken along line 2—2 of FIG. 1.

The fluid sampler preferably includes a plurality of syringes 5, which enables fluid sampler 100 to obtain multiple fluid samples, each syringe 5 drawing fluid at the same or at different times. FIG. 2 is a view of the sampler taken along line 2—2 of FIG. 1, showing an arrangement of ten syringes 5 placed within the internal circumference of the housing 1. Control device 6 and power source 7 are also shown.

FIG. 1 shows syringe 5 connected in-line with tubing 16 to a solenoid valve 17. Solenoid valve 17 can be in an open or closed position. Solenoid valve 17 is normally in a closed position and forms a watertight seal that prevents entry of fluid into the base of syringe 5. Solenoid valve 17 preferably responds to an electrical triggering signal from control device 6, the triggering signal preferably transmitted through connecting wires 18. The control device 6 can be powered by power source 7, such as a 12 V battery. By opening valve 17, a passageway is achieved between the outside surrounding environment and the internal reservoir 11 inside the syringe 5.

The structure for drawing fluid is powered by stored potential energy within the sampler. In the embodiment shown in FIG. 1, the structure for drawing fluid includes a spring-loaded syringe 5 attached to a solenoid valve 17. In practice, the potential energy in the spring is harnessed and remains trapped until released by the solenoid valve 17. To prepare the system for sample collection, the solenoid valve 17 is placed in the open position. The spring 15 is then compressed by pushing on mounting base 14 until the stopper 10 is all the way to the bottom of syringe 5. With the spring 15 thus compressed and the stopper 10 in the bottom of the syringe, the solenoid valve 17 is then closed, creating a vacuum that holds the stopper 10 at the base of the syringe 5. Thus, the potential energy remains trapped in the compressed spring as long as the solenoid valve 17 is closed. Upon opening of the solenoid valve 17, a passageway is created to the outside environment. Energy stored in the spring 5 is then released, creating distance between the stopper 10 and syringe bottom 9, thereby drawing fluid, e.g. water, into the internal reservoir 11. Once the desired volume of fluid is withdrawn, the control device 6 signals the valve 17 to close, thus sealing the fluid sample.

Although fluid sampler 100 uses a solenoid valve 17 and an electrical signal, any suitable valve could be used along with any triggering signal.

While the spring 15 shown in FIG. 1 uses release of mechanical potential energy to draw fluid, any form of stored energy, or other arrangements for creating a vacuum, can be used to increase the volume of the internal reservoir 11. The vacuum only generally needs to be a relative vacuum. For example, a volume sealed at ambient pressure can provide a relative vacuum sufficient to power water sampling at a given depth of water.

The structure for drawing fluid can further include one or more filter assemblies. Connected with the syringe bottom 9 is a substantially rigid tubing 16 which connects the internal cavity 11 of the syringe 5 to the environment surrounding fluid sampler 100. Tubing 16 can provide fluid connection between a plurality of optional components and syringe 5. For example, an in-line filter 19 may be disposed in rigid tubing 16 to remove undesired material from the sample. Additionally, pre-filters made of various materials suited for a particular purpose can be disposed over the open ends of tubing 16 at the sites of contact with the external environment. An optional chamber 23 containing agents for preserving the sample can be connected to tubing 16.

Fluid sampler 100 also preferably includes a clock (not shown), such as a real-time clock. A clock can provide time information to trigger the microprocessor 6 to direct the taking of one or more samples at desired times. The time information can be preprogrammed and stored in a suitable memory, or received from an external source.

One function of the control device 6 can be to transmit an actuating signal to control the triggering of the collection process. This enables the sampler to be fully automatic and self-contained. Embodiments of the sampler thus equipped can operate in remote geographic locations, for example for several years, without need for any maintenance or observation.

In embodiments of the invention utilizing solenoid valves 17, an amplifier, such as a metal oxide semiconductor field effect transistor (MOSFET) can be used to amplify microprocessor signal when the signal does not provide sufficient current to activate the solenoid valve 17 on its own. In the case of solenoid valves 17, the activation signal can be a magnetic field that is established when the current signal provided passes through a coil included in valve 17.

The duration of the fluid flow through the open passageway, i.e., the period of time during which the solenoid valve is open, is a programmable value determined by the control device 6. Options to increase "dwell time," for example to accommodate longer filling periods required by viscous samples, can be programmed into the control device 6.

In some embodiments of the sampler, a real time clock can be included in conjunction with the microcomputer or microprocessor, and used to initiate fluid collection at preprogrammed times. An electronic memory (not shown) can also be included, such as a random access memory (RAM). The memory is preferably a non-volatile memory. Typically, as is standard in the art, power management of the device is minimized by setting the microprocessor 6 in "sleep mode" most of the time, with "wake up" intervals set to occur only as appropriate, for example every few seconds, to determine whether or not it is time to take a sample. Accordingly, very small amounts of energy are used to control the operation of the sampler 100. For example, it is estimated that a 12 volt battery would contain enough power to run a sampler according to the invention for at least 12 years, and possibly as long as 30 years without the need for battery replacement.

In some embodiments, the fluid sampler 100 can also include at least one sensor 22 communicably connected to the microcomputer or microprocessor 6. In the embodiment shown in FIG. 1, a sensor 22 is shown on the external aspect of housing 1. However, the sensor 22 can be located either inside the sealed housing 1, with a sealed extension communicating with the outside environment, or situated outside the sealed housing 1. In a typical water sampling application, the sensor 22 can be a pH sensor, a probe that senses temperature, conductivity (salinity) or dissolved oxygen, or an ion selective electrode or solute probe.

In some versions of the invention including sensors 22, fluid collection can be initiated by a signal from the sensor 22. For example, signals from the sensor 22 can initiate fluid collection upon an environmental parameter reaching a specified level. The sensor 22 can be adapted to detect physical characteristics of the fluid environment external to the sampler 100, for example pH, temperature, dissolved oxygen levels, conductivity, salinity and ionic concentration.

The sensor 22 can relay the environmental information to the control device 6, which can then send a signal to trigger sample collection. For example, a microprocessor or microcomputer 6 can be programmed to activate one or more fluid sampling structures 5 upon detection by the sensor 22 of a selected external condition, such as a reduction in the salinity of a water sample below a designated level. The microprocessor or microcomputer 6 is preferably adapted to process and store information obtained from the sensor 22, such as environmental conditions and the time of fluid sampling.

Some versions of the invention further provide for remote sampling situations in which it may be desirable to initiate sample collection based on an external command. For example, it may be desirable to analyze for pollutants in a body of water immediately after it is recharged with runoff from the surrounding land following a rainstorm. Due to the unpredictability of the timing of rainfall in a particular area, it may be advantageous to relay a command to the sampler to take a sample at a precise time (such as 20 minutes after the start of rainfall), once the rainfall information becomes available, for example by reference to local weather sensing technology, such as radar. To accommodate such needs, the fluid sampler 100 can include at least one antenna 21, the antenna 21 adapted for receiving a wireless activating signal from an external source. Referring to FIG. 1, in embodiments adapted for receiving such signals, a receiving device 20, operably connected to an antenna 21 and control device 6, can be included within housing 1. Sample collection can be triggered upon receipt of a signal communicated by a wireless communication device by antenna 21 and receiving device 20, connected thereto. In other applications, communications from an external device can, for example, provide an updated schedule of sample collection dates and times, for upload to the microprocessor memory of the control device 6.

Although the antenna 21 is shown inside the housing 1 in FIG. 1, those of ordinary skill in the art will appreciate that the antenna 21 can be disposed outside of the housing 1. Typically, in applications in which the sampler is deployed in water deeper than several inches for RF communications, the antenna 21 is preferably positioned above the water level, for example secured to a buoy marking the site of the underwater sampling location. The remotely disposed antenna 21 can be connected to receiver 20 through a standard insulated wired connection or suitable alternative connection.

In some embodiments, receiver 20 can be a transceiver. This allows the fluid sampler 100 to both receive wireless transmissions from outside of the sampler 100 and to send wireless signals to at least one device located outside the sampler 100. For example, when receiving device 20 is a transceiver it can transmit communications, such as activating signals, to remotely located samplers.

In another aspect, the invention provides a fluid sampling system including a plurality of fluid samplers. When deployed as an array or grid of fluid samplers, one fluid sampler can serve as a master control unit receiving wireless transmissions and relaying instructions to the other (slave) sampling fluid samplers through a suitable connection, such as a wire or fiber optic connection.

The invention further provides a fluid sampling system including a plurality of fluid samplers connected together to form a chain or grid that can sample a water column in both time and space. Within the system, at least one of the samplers can be a master sampler including at least one antenna and a transceiver connected to the antenna. The master sampler can be adapted to receive wireless transmissions from remote locations, and to send communications to at least one location outside of the sampler. Typically, the master sampler would relay instructions to other (slave) samplers within the system. Communication by the master to the slave samplers can be either through wireless communication, or through wire or fiber optic connections. Typically, wire or fiber optic connections would be suitable for interconnections between submerged samplers, such as slaves deployed underwater in a grid or array.

Overall, the fluid sampler can be provided at a low cost, can be relatively small, and easy to operate. The sampler also permits sampling from a wide range of potential sampling sites, such as groundwater, lakes, rivers, estuaries and oceans, and can further provide the ability to receive, store and transmit sampling information. Due to the modular components which can be used within the system, construction of the samplers and the sampler system can be automated and fabricated.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A fluid sampler comprising:
    a substantially watertight housing, and
    at least one spring-loaded syringe that stores potential energy operably connected to at least one solenoid valve that operates to release said stored potential energy, said spring-loaded syringe and said solenoid valve both contained at least partially within said housing, said spring-loaded syringe drawing fluid from outside of said housing using said stored potential energy.

2. The fluid sampler of claim 1, wherein said fluid sampler further comprises a filter assembly.

3. The fluid sampler of claim 1, wherein said housing is substantially airtight.

4. The fluid sampler of claim 1, further comprising a control device for issuing electronic activating signals, wherein said activating signals applied to said solenoid valve results in fluid being drawn into said spring-loaded syringe.

5. The fluid sampler of claim 4, wherein said control device is a microprocessor or a microcomputer.

6. The fluid sampler of claim 5, further comprising at least one of an electronic memory and a clock.

7. The fluid sampler of claim 5, further comprising at least one sensor, said sensor communicably connected to said microcomputer or said microprocessor.

8. The fluid sampler of claim 7, wherein said at least one sensor is selected from the group consisting of a pH sensor, a temperature sensor, a dissolved oxygen probe, a conductivity sensor, a salinity sensor and an ion selective electrode.

9. The fluid sampler of claim 7, wherein fluid collection can be initiated by a signal from said sensor.

10. The fluid sampler of claim 7, wherein said sampler includes a memory, said microprocessor or microcomputer processing and storing information from said sensor.

11. The fluid sampler of claim 10, wherein said stored information comprises environmental conditions present at times of fluid sampling.

12. The fluid sampler of claim 5, further comprising at least one antenna, said antenna adapted for receiving a wireless activating signal.

13. The fluid sampler of claim 12, further comprising a receiving device connected to said antenna, said receiving device adapted to receive wireless transmissions from outside of said housing.

14. The fluid sampler of claim 12, further comprising a transceiver for sending wireless signals to at least one location outside of said housing.

15. The fluid sampler of claim 1, wherein said solenoid valve when closed seals said fluid drawn from outside of said housing inside said spring-loaded syringe.

16. A fluid sampling system, comprising:
a plurality of fluid samplers, said fluid samplers each including a substantially watertight housing, and at least one spring-loaded syringe that stores potential energy operably connected to at least one solenoid valve that operates to release said stored potential energy, said spring-loaded syringe and said solenoid valve both contained at least partially within said housing, said spring-loaded syringe drawing fluid from outside of said housing using said stored potential energy,
wherein at least one of said plurality of fluid samplers is a master sampler, said master sampler including at least one antenna and a transceiver connected to said antenna.

17. The fluid sampling system of claim 16, wherein said master sampler relays instructions to and from other of said plurality of fluid samplers.

18. The fluid sampling system of claim 16, wherein said solenoid valve when closed seals said fluid drawn from outside of said housing inside said spring-loaded syringe.

19. A method for sampling fluids comprising the steps of:

providing a substantially watertight housing and at least one spring-loaded syringe that stores potential energy operably connected to at least one solenoid valve that operates to release said stored potential energy, said spring-loaded syringe and said solenoid valve both contained at least partially within said housing, and drawing said fluid from outside of said housing into said spring-loaded syringe using said stored potential energy.

20. The method of claim 19, further comprising the step of sealing said fluid inside said spring-loaded syringe through actuation of said solenoid valve.

* * * * *